United States Patent
Mikszta et al.

(10) Patent No.: US 7,731,968 B2
(45) Date of Patent: *Jun. 8, 2010

(54) TOPICAL DELIVERY OF VACCINES

(75) Inventors: John A. Mikszta, Durham, NC (US); John M. Brittingham, Wake Forest, NC (US); Jason Alarcon, Raleigh, NC (US); Ronald J. Pettis, Durham, NC (US); John P. Dekker, III, Cary, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/851,956

(22) Filed: Sep. 7, 2007

(65) Prior Publication Data

US 2008/0009785 A1    Jan. 10, 2008

Related U.S. Application Data

(63) Continuation of application No. 10/436,757, filed on May 13, 2003, now abandoned, which is a continuation of application No. 09/576,643, filed on May 22, 2000, now Pat. No. 6,595,947.

(51) Int. Cl.
   *A61K 39/00*    (2006.01)
   *A61K 47/00*    (2006.01)
   *A61K 9/00*    (2006.01)
   *A61K 9/14*    (2006.01)

(52) U.S. Cl. ................ 424/184.1; 424/278.1; 424/400; 424/489; 514/44 R

(58) Field of Classification Search ...................... None
See application file for complete search history.

(56) References Cited

U.S. PATENT DOCUMENTS

| | | | |
|---|---|---|---|
| 3,289,670 A | 12/1966 | Kurg et al. | |
| 3,351,059 A * | 11/1967 | Kravitz ........................ | 604/46 |
| 3,556,080 A | 1/1971 | Hein | |
| 3,964,482 A | 6/1976 | Gerstel et al. | |
| 4,270,548 A | 6/1981 | Brennan | |
| 4,483,348 A | 11/1984 | Sher | |
| 4,568,343 A | 2/1986 | Leeper et al. | |
| 4,746,515 A | 5/1988 | Cheng et al. | |
| 5,003,987 A | 4/1991 | Grinwald | |
| 5,273,528 A | 12/1993 | Skeen et al. | |
| 5,380,337 A | 1/1995 | Romaine | |
| 5,501,784 A | 3/1996 | Lessmollmann et al. | |
| 5,611,806 A | 3/1997 | Jang | |
| 5,620,896 A | 4/1997 | Hermann et al. | |
| 5,658,515 A | 8/1997 | Lee et al. | |
| 5,660,680 A | 8/1997 | Keller | |
| 5,679,647 A | 10/1997 | Carson et al. | |
| 5,848,991 A | 12/1998 | Gross et al. | |
| 5,855,801 A | 1/1999 | Lin et al. | |
| 5,879,326 A | 3/1999 | Godshall et al. | |
| 5,885,211 A | 3/1999 | Eppstein et al. | |
| 5,910,306 A | 6/1999 | Alving et al. | |
| 5,919,364 A | 7/1999 | Lebouitz et al. | |
| 5,928,207 A | 7/1999 | Pisano et al. | |
| 5,931,794 A | 8/1999 | Pitesky | |
| 5,958,589 A | 9/1999 | Glenn et al. | |
| 5,964,729 A | 10/1999 | Choi | |
| 5,970,998 A | 10/1999 | Talbot et al. | |
| 5,980,898 A | 11/1999 | Glenn et al. | |
| 5,983,136 A | 11/1999 | Kamen | |
| 6,015,599 A | 1/2000 | Keller et al. | |
| 6,032,060 A | 2/2000 | Carim et al. | |
| 6,050,988 A | 4/2000 | Zuck | |
| 6,065,864 A | 5/2000 | Evans et al. | |
| 6,106,751 A | 8/2000 | Talbot et al. | |
| 6,132,755 A | 10/2000 | Eicher et al. | |
| 6,173,202 B1 | 1/2001 | Eppstein | |
| 6,183,434 B1 | 2/2001 | Eppstein | |
| 6,187,210 B1 | 2/2001 | Lebouitz et al. | |
| 6,256,533 B1 | 7/2001 | Yuzhakov et al. | |
| 6,299,900 B1 | 10/2001 | Reed et al. | |
| 6,312,612 B1 | 11/2001 | Sherman et al. | |
| 6,331,266 B1 | 12/2001 | Powell et al. | |
| 6,334,856 B1 * | 1/2002 | Allen et al. .................. | 604/191 |
| 6,454,755 B1 | 9/2002 | Godshall | |
| 6,623,457 B1 * | 9/2003 | Rosenberg .................. | 604/191 |
| 6,835,184 B1 * | 12/2004 | Sage et al. ................... | 604/46 |

FOREIGN PATENT DOCUMENTS

| | | |
|---|---|---|
| EP | 0381410 | 8/1990 |
| EP | 05091222 | 4/1994 |
| EP | 1086719 | 3/2001 |
| EP | 1092444 | 4/2001 |
| GB | 2125280 | 8/1924 |
| RU | 1724181 | 4/1994 |
| WO | WO9607369 | 3/1996 |
| WO | WO9703718 | 2/1997 |
| WO | WO9711650 | 4/1997 |
| WO | WO9748440 | 12/1997 |
| WO | WO9748442 | 12/1997 |
| WO | WO9900155 | 1/1999 |
| WO | WO9943350 | 9/1999 |

OTHER PUBLICATIONS

Degano et al., "Intradermal DNA Immunization of mice against influenza A virus using the novel Powderject system," Vaccine, vol. 16, No. 4 (1998).

(Continued)

Primary Examiner—Mary E Mosher
(74) Attorney, Agent, or Firm—Robert E. West

(57) ABSTRACT

The present invention provides improved methods for delivery of substances into the skin. It has been discovered that delivery of substances such as nucleic acids, amino acids, amino acid derivatives, peptides and polypeptides simultaneously with abrasion of the skin enhances delivery and the biological response as compared to application of the substance to previously abraded skin.

13 Claims, 4 Drawing Sheets

OTHER PUBLICATIONS

Iwasaki et al., "Epitope-specific cytoxic T lymphocyte induction by minigene DNA immunization," Vaccine 17(15-16):2081-8 (1999).

Robinson, "DNA vaccines: basic mechanism and immune responses," Int J Mold Med 4(5):549-55 (1999).

Definition from Wikipedia, Apr. 22, 2006.

MJ. McCluskie et al., Molecular Medicine, 5:287, 1999.

Skin Immunization Made Possible by Cholera Toxin, Nature, vol. 391, Feb. 26, 1998,p. 851.

Tuberculin, Old Mno-Vacc Test (O.T.), product information, www.us.aventispasteur.com., (1991).

E.Raz et al., Intradermal Gene Immunization: The Possible Role of DNA Uptake in the Induction of Cellular Immunity to Viruses, Proc. Natl.Acad. Sci., USA 91 (1994).

D.A. Greenhalgh et al., Epidermis: An Attractive Target Tissue for Gene Therapy, Journal of Investigative Dermatology, vol. 108, No. 5, May 1997.

M. Yokohama et al., DNA Immunization: Effects of Vehicle and Route of Administration on the Induction of Protective Antriviral Immunity, FEMS Immunology and Medical Microbioligy 14 (1996) 221-230.

L. Li et al., the Feasibility of Targeted Selective Gene Therapy of the Hair Follicle, Nature Medicine, vol. 1, No. 7, Jul. 1995, p. 705-706.

D. Tang, Vaccination onto Bare Skin, Nature, vol. 388, Aug. 21, 1997, p. 729.

Wm.C.Brown Publishers, Van De Graff, et al., Concepts of Human Anatomy and Physiology, pp. 197-1999 (1986) USA.

* cited by examiner

TOPICAL DELIVERY OF VACCINES

This Application is a continuation of application Ser. No. 10/436,757 filed May 13, 2003, now abandoned which is a continuation of application Ser. No. 09/576,643 filed May 22, 2000, now Patented as U.S. Pat. No. 6,595,947.

FIELD OF THE INVENTION

This Invention relates to topical delivery of substances into the skin, particularly by disruption of the stratum corneum and delivery of the substance to the epidermal layer beneath.

BACKGROUND OF THE INVENTION

Delivery of substances to the body through the skin has typically been invasive, involving needles and syringes to facilitate intradermal (ID), intramuscular (IM) or subcutaneous (SC) injection. These methods are painful for the subject, require the skills of a trained practitioner and often produce bleeding. There have more recently been efforts to overcome these disadvantages by use of devices which disrupt or abrade the stratum corneum, the thin external layer of keratinized cells about 10-20 µm thick which serves as the skin's outer barrier, with delivery of the desired substance to the exposed epidermis. The substance can then diffuse through the epidermis to the dermis which contains blood vessels and lymphatics for absorption and delivery of the substance throughout the body. For topical delivery of vaccines, the epidermis itself is a particularly desirable target for drug delivery as it is rich in antigen presenting cells. In comparison, the dermis contains fewer antigen presenting cells. The stratum corneum and epidermis do not contain nerves or blood vessels, so this method has the advantage of being essentially painless and blood-free while giving access to the skin layers capable of responding to the antigen.

The prior art reports a variety of devices and methods for disrupting the stratum corneum for the purpose of delivering substances to the body. For example, breach of the stratum corneum may be achieved by puncturing as taught in U.S. Pat. No. 5,679,647 to Carson, et al. This patent teaches that narrow diameter tynes, such as those found on devices used for tuberculin skin tests and allergy tests, can be coated with polynucleotides and used for delivery of such materials into the skin. The method of using such devices involves puncturing the skin with the tynes resulting in intracutaneous injection of the coated substance. This is in contrast to the present invention, where it has been unexpectedly discovered that substances coated onto the surface of narrow diameter microprotrusions are delivered more effectively by lateral abrasion across the skin surface rather than by puncturing. U.S. Pat. No. 5,003,987; U.S. Pat. No. 5,879,326; and U.S. Pat. No. 3,964,482 teach breaching the stratum corneum by abrasion, however, little is known about how to optimize topical application methods to achieve efficient and efficacious delivery by this route. Such optimization is of particular interest for topical nucleic acid delivery, especially topical delivery of nucleic acid-based vaccines and gene therapies. In this regard, the most commonly suggested method for topical administration is to abrade the skin prior to application of the vaccine. However, it has now been unexpectedly found that delivery of nucleic acids and peptides or polypeptides such as allergens is more efficient and more efficacious when the substance is delivered simultaneously with abrasion.

SUMMARY OF THE INVENTION

The present invention provides optimized methods for topical delivery of substances, particularly nucleic adds, amino acids, amino acid derivatives, peptides or polypeptides. It has been discovered that nucleic adds exhibit enhanced gene expression and produce an enhanced immune response to the expressed protein when they are delivered simultaneously with abrasion of the stratum corneum. Similarly, allergens delivered simultaneously with abrasion produce a more vigorous immune response than conventional allergen testing methods.

DETAILED DESCRIPTION OF THE INVENTION

Figure 1:
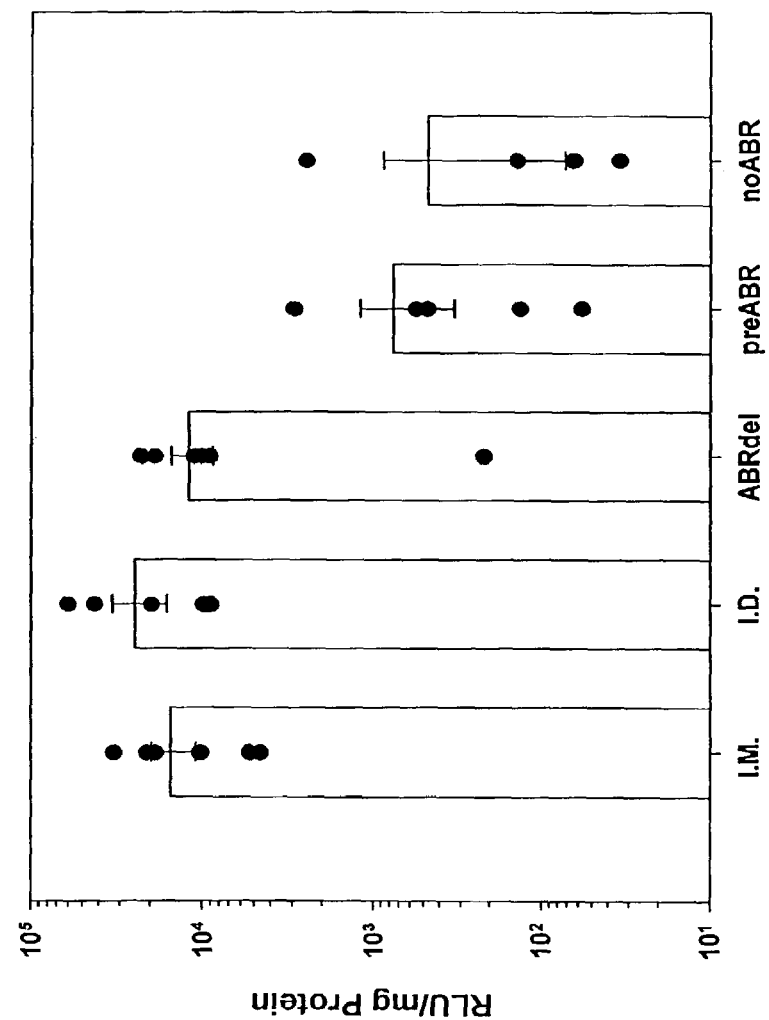
FIG. 1 illustrates levels of gene expression obtained with the various nucleic add delivery protocols tested in Example 1.

The term "abrasion" as used herein refers to disruption of the outer layers of the skin, for example by scraping or rubbing, resulting in an area of disrupted stratum corneum. This is in contrast to "puncturing" which produces discrete holes through the stratum corneum with areas of undisrupted stratum corneum between the holes. According to the methods of the invention, substances such as nucleic acid-based vaccines and peptides or polypeptides are applied to the skin simultaneously with abrasion rather than being applied to previously abraded skin. That is, the substance is abraded into the skin rather than being passively applied to skin which has been previously abraded. This method results in improved delivery and response as compared to post-abrasion application.

The substance may be delivered into the skin in any pharmaceutically acceptable form, but a liquid or gel formulation is preferred. In one embodiment the substance is applied to the skin and an abrading device is then moved or rubbed reciprocally over the skin and the substance. It is preferred that the minimum amount of abrasion to produce the desired result be used. Determination of the appropriate amount of abrasion for a selected substance is within the ordinary skill in the art. In another embodiment the substance may be applied in dry form to the abrading surface of the delivery device prior to application. In this embodiment, a reconstituting liquid is applied to the skin at the delivery site and the substance-coated abrading device is applied to the skin at the site of the reconstituting liquid. It is then moved or rubbed reciprocally over the skin so that the substance becomes dissolved in the reconstituting liquid on the surface of the skin and is delivered simultaneously with abrasion. Alternatively, a reconstituting liquid may be contained in the abrading device and released to dissolve the substance as the device is applied to the skin for abrasion. It has been found that nucleic add preparations may also be coated on the abrading device in the form of a gel, although the improvement in gene expression is not as significant as in certain other embodiments of the invention.

Any device known in the art for disruption of the stratum corneum by abrasion can be used in the methods of the invention. These include, for example, miroelectromechanical (MEMS) devices with arrays of short microneedles or microprotrusions, sandpaper-like devices, scrapers and the like. If the abrading device does not include a reservoir for containment and discharge of fluids from the device, the substance-containing liquid or the reconstituting liquid must be separately applied to the skin prior to abrading, for example from a separate dispenser or pump. However, reservoirs may be an integral part of the abrading device. Typically the reservoir is in fluid communication with the abrading surface of the device, for example via channels through the needles or protrusions, or via channels which exit the reservoir between such needles or protrusions, or via porous materials. In this embodiment, the substance or reconstituting liquid is contained in the reservoir of the abrading device and is dispensed to the skin surface prior to abrasion or simultaneously with abrasion. The abrading device may also include means for controlling the rate of delivery of the substance or reconstituting liquid, or for controlling the amount of substance or reconstituting liquid delivered.

Nucleic acids for use in the methods of the invention may be RNA or DNA. They may be in any physical form suitable for topical administration and for uptake and expression by cells. It may be contained in a viral vector or liposome, or it may be delivered as a free polynucleotide such as a plasmid as is known in the art. The nucleic acid will typically be formulated in a pharmaceutically acceptable formulation such as a fluid or gel which is compatible with the nucleic acid. Pharmaceutically acceptable peptide and polypeptide formulations for use in the invention, including formulations for allergen compositions, are also well known in the art.

It has been found that minimal abrasion (as little as one pass over the skin) is sufficient to produce an improvement in nucleic acid delivery to skin cells. The amount of nucleic acid delivery and expression continues to increase with increasing numbers of abrasive passes over the skin. Six abrasive passes or more gave the maximum improvement in nucleic acid delivery in our experimental systems. Although all abrasive passes over the skin may be in the same direction, it is preferred that the direction be altered during abrasion. The most commonly used protocol for delivery of nucleic add vaccines today is IM injection, usually with additional response enhancers when the dose is low. Determination of the appropriate dose of nucleic acid vaccine to be delivered using the methods of the invention is within the ordinary skill in the art. However, it is an advantage of the inventive methods that delivery of nucleic add vaccines is more efficient than IM delivery even without response enhancers, as evidenced by levels of gene expression and stimulation of an immune response.

Amino adds, amino add derivatives, peptides and polypeptides, particularly allergens, may also be delivered topically according to the methods of the invention. Allergens are conventionally delivered into the skin by intracutaneous puncture using devices similar to the tuberculin tyne test. However, it has been unexpectedly found that an enhanced allergenic response can be obtained by simultaneous abrasion and delivery. This produces a more sensitive test and has the advantage that a minor or imperceptible response to the conventional allergen test may be more easily detected using the methods of the invention.

EXAMPLE 1

Delivery of Plasmid DNA Using a Solid Microneedle Array

Plasmid DNA (35 µg) encoding firefly luciferase was administered to anesthetized BALB/c mice by IM injection or ID injection with a standard 30 g needle and 1 cc syringe, or was administered topically using a 200 µm silicon microneedle array. Two protocols were used for DNA administration using the microneedle array:
1) Simultaneous abrasion and delivery (ABRdel): Mice were shaved on the caudal dorsum using electric clippers, followed by a No. 10 scalpel blade to remove remaining hair. The DNA solution was then applied to a 1 cm$^2$ site on the skin surface and the microneedle array was placed in contact with this solution and moved laterally in alternating direction six times across the skin surface (three passes in each direction). The DNA solution was left to air dry and the skin site was left uncovered until skin biopsies were recovered.
2) Pre-abrasion (preABR): After shaving as described above, a 1 cm$^2$ site was pre-abraded by lateral movement of the microarray across the skin surface six times with alternating direction (three passes in each of two directions). The DNA solution was then spread over the abraded skin surface and left to air dry as above.

As a control for possible DNA delivery through hair follicles or nicks resulting from the shaving process, animals were shaved as above but were not abraded with the microarray (noABR). The DNA solution was applied topically to the 1 cm$^2$ shaved skin site and left to air dry.

In all groups, tissue samples were collected 24 hr. after DNA administration. Tissue homogenates were analyzed for luciferase activity using a luminescence assay. All samples were normalized for total protein content, as determined by a standard BCA protein assay. Data were expressed as Relative Light Units (RLU) per mg of total protein and results are shown in FIG. 1. Each symbol represents the response of a single mouse. Cumulative data from two separate experiments are shown (n=6 for each group). The levels of luciferase gene expression attained following ABRdel were similar in magnitude to needle-based IM and ID injections and significantly greater (p=0.02) than for topical delivery onto preabraded or unabraded skin.

EXAMPLE 2

Correlation of Delivery with Number of Abrasive Passes

Luciferase plasmid DNA (35 µg) was administered by ABRdel as described in Example 1, but the number of lateral passes of the device across the skin surface was varied (12, 10, 6, 4 and 2 times). In addition, after placing the DNA solution on the surface of shaved but unabraded skin, the microneedle array was repetitively pressed against the skin (six times) to simulate puncture-mediated delivery. Topical application of the DNA solution in the absence of abrasion (noABR) was included as a control for possible DNA delivery through hair follicles or nicks. Skin biopsies (1 cm$^2$) were collected 24 hr. after application and were assayed for luciferase activity as described in Example 1.

Figure 2:
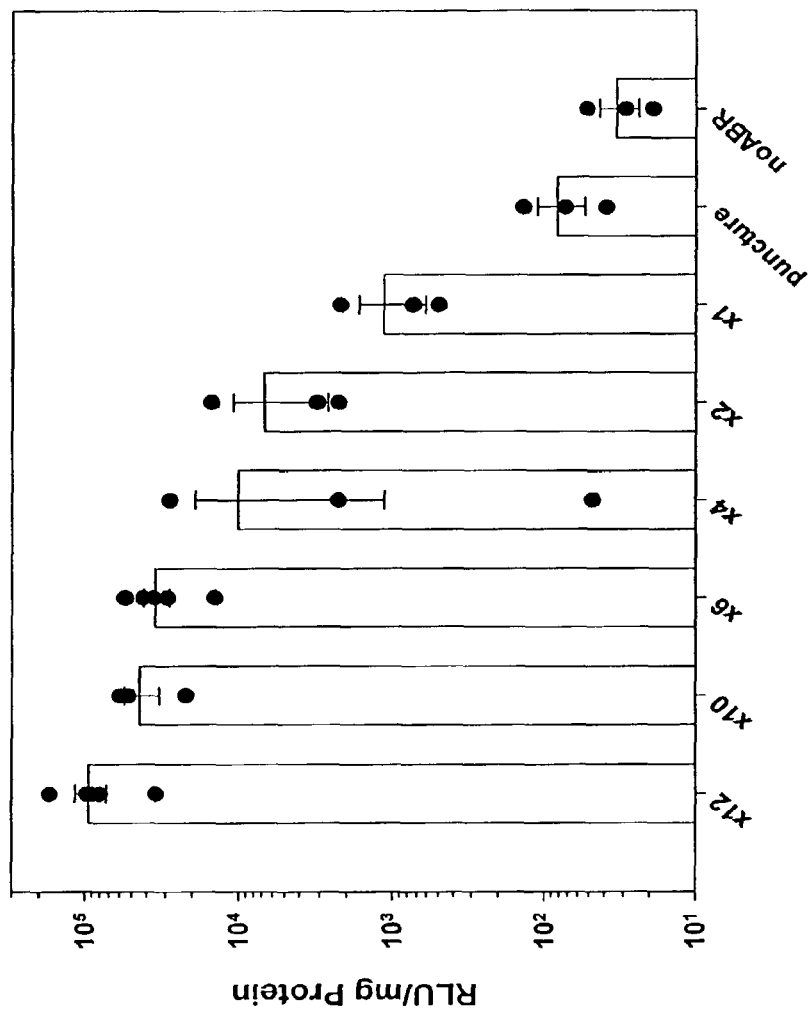
FIG. 2 illustrates levels of gene expression obtained by varying the number of abrasions as described in Example 2.

The results are illustrated in FIG. 2. Each symbol represents the response of a single mouse, and n=3 for all groups except for "x12" and "x6" in which n=5. Increasing levels of gene expression were attained with increasing numbers of passes of the microneedle array across the skin surface. Mean levels of expression ranged from greater than 1,000- to 2,800-fold above noABR controls in groups treated by six or more abrasions. Mean responses following 4, 2, or 1 pass of the device across the surface of the skin were about 300-, 200- and 30-fold above background, respectively. Mean levels of expression in the "puncture" group were only 2-fold above background and were not significantly different from noABR controls.

These data demonstrate that the abrasion process is a critical component of topical delivery of DNA into the skin. Increased levels of gene expression were attained by increasing the number of abrasive passes of the abrader device, although gene expression was observed after even a single pass. In addition, laterally rubbing or abrading the skin significantly increased nucleic acid delivery and gene expression as compared to repetitively pressing the microneedle array against the skin without lateral abrasion.

EXAMPLE 3

Formulation of Nucleic Acid Vaccines

Luciferase plasmid (35 µg) was administered as a liquid formulation by ID injection or by simultaneous abrasion and delivery ("ABRdel liquid") with six passes of the microneedle device across the skin surface as described in Example 1. In addition, the DNA was lyophilized to a powder and coated onto the surface of the microneedle array and administered by simultaneous abrasion and delivery either directly as a powder ("ABRdel powder") or upon reconstitution in PBS buffer at the time of application ("ABRdel powder/recon"). Reconstitution was accomplished by placing the powder-coated array in direct contact with a droplet of PBS on the surface of the skin, followed by simultaneous abrasion and delivery. Microneedle arrays were also coated with DNA dissolved in 0.5% agarose gel and administered by simultaneous abrasion and delivery as described above ("ABRdel gel"). Topical application of the liquid formulation in the absence of abrasion (noABR) was included as a control. Skin biopsies (1 cm$^2$) were collected 24 hr. after application and were assayed as described in Example 1.

Figure 3:
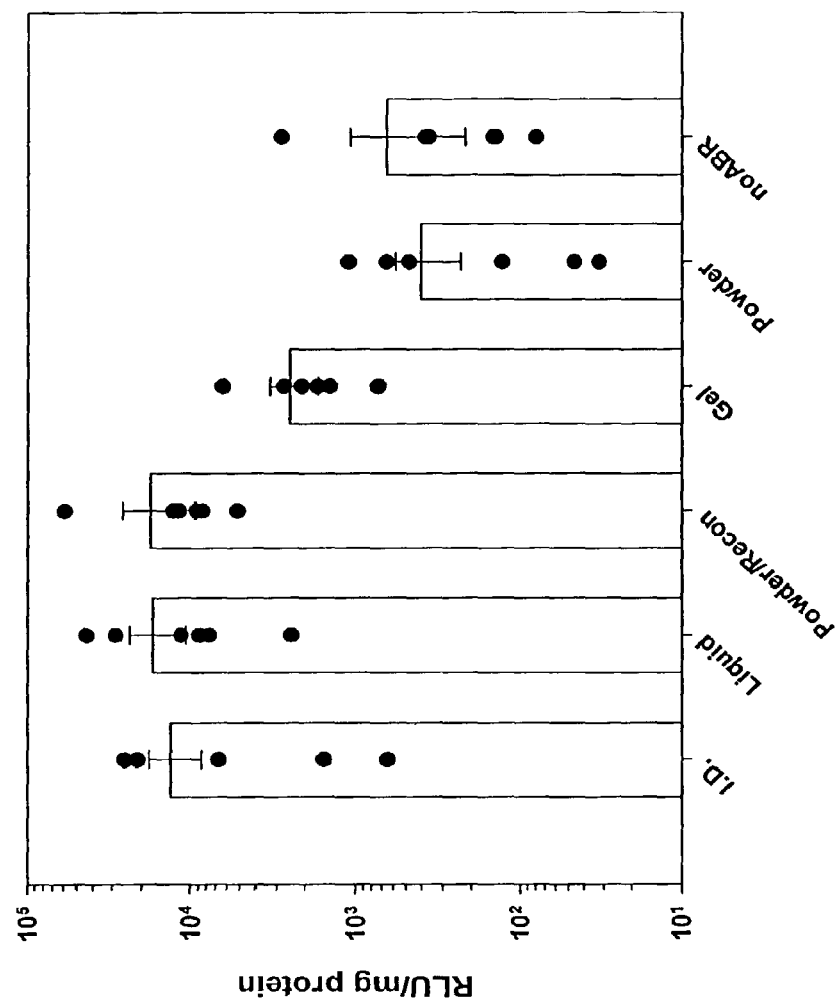
FIG. 3 illustrates levels of gene expression obtained by varying the formulation of the nucleic acid and the delivery protocol as described in Example 3.

The results are shown in FIG. 3. Each symbol represents the response of a single mouse. Cumulative data from two separate experiments are shown, where n=6 for each group. Similar levels of luciferase expression in the skin (about 20-30 fold above noABR) were observed for the ID injection, ABRdel liquid and ABRdel powder/recon groups. Although neither direct delivery of gel or powder-coated DNA without reconstitution resulted in gene expression statistically above the noABR control, responses following direct gel-based delivery were about 2-10 fold higher than the mean control response. These results demonstrate that reconstitution of a dry form of the vaccine at the time of simultaneous abrasion and delivery produces results comparable to simultaneous abrasion and delivery of a liquid vaccine formulation. This has advantages for commercial application of the methods, as an abrader device with a liquid-filled reservoir could be pre-coated with the vaccine powder for reconstitution of the vaccine as it is applied by abrasion.

EXAMPLE 4

Antibody Response to Topical Delivery of Plasmid DNA

Plasmid DNA encoding the Hepatitis B surface antigen (HbsAg) was administered to anaesthetized BALB/c mice by IM or ID injection with a standard 30 g needle and 1 cc syringe, or was administered topically using a 200 µm silicon solid microneedle array according to the ABRdel protocol of Example 1. Mice were given a total of three immunizations of 100 µg per dose. Serum samples were analyzed by ELISA for antibodies to HbsAg (total Ig) 2-3 weeks following each immunization. DNA was applied topically to shaven but unabraded (noABR) skin as control for possible delivery through nicks or hair follicles. Data represent an anti-HbsAg titer, defined as the highest dilution of a serum sample yielding absorbance values at least three times above background (serum obtained from naïve, unimmunized mice).

Figure 4:
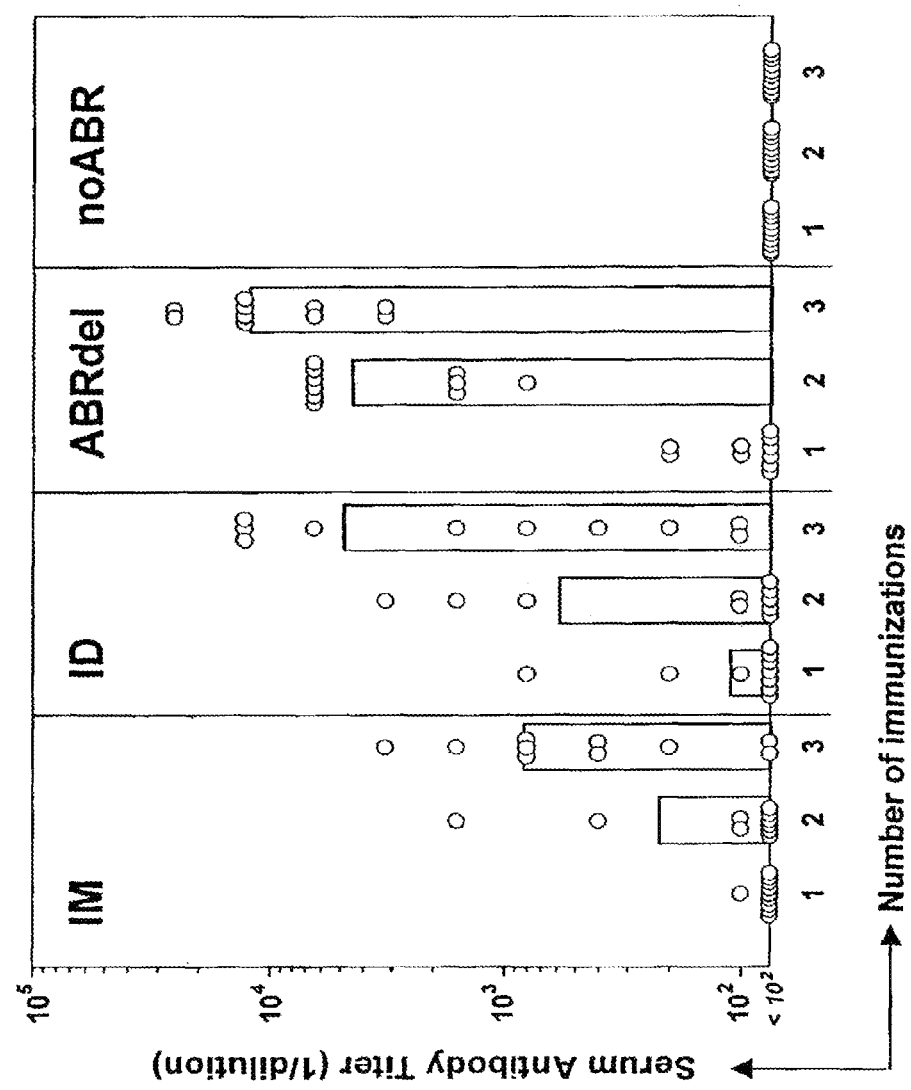
FIG. 4 illustrates the antibody response following topical delivery of plasmid DNA as described in Example 4.

A total of ten mice per group were analyzed. Mean titers are represented as bars in FIG. 4, With the responses of individual mice indicated as open symbols. The results indicate that the ABRdel protocol induces strong serum antibody responses in vivo. The magnitude of such responses were significantly greater ($p<0.05$ after immunizations 2 and 3) than those induced via either IM (the current standard for DNA-based vaccine delivery) and ID injections. In addition, the responses following ABRdel were considerably less variable than those observed following either standard needle-based injection route. Mean titers after three immunizations were 12,160 for the ABRdel group, compared to 820 following IM injection and 4800 via ID injection. Notably, the ABRdel approach was the most effective delivery route following two Immunizations; 100% (10/10) of animals treated via ABRdel seroconverted after two immunizations, compared to 40% (4/10) via the IM route and 50% (5/10) via ID injection. None of the animals administered plasmid DNA topically in the absence of abrasion mounted a detectable antibody response. Further characterization of the antibody isotypes revealed that ABRdel induces a similar mixed response as standard needle-based IM and ID injections, consisting of both IgG1 and IgG2a. These results are in contrast to previously described intradermal vaccinations using the gene gun, in which antibody responses consisted exclusively of IgG1 in the absence of IgG2a (e.g., see McCluskie, M J et al., Molecular Medicine 5:287, 1999).

EXAMPLE 5

Topical Delivery of Allergens

Histamine dihydrochloride (2.5 mg) was administered to the skin of anaesthetized swine by simultaneous abrasion and delivery using a 200 µm silicon solid microneedle array, as described in Example 1 (ABRdel; 4 passes of the device across the skin surface). The histamine was formulated either as a liquid or as a lyophohzed powder which was coated onto the surface of the microarray and reconstituted in water directly on the skin at the time of application. For comparison, histamine solution was placed as a droplet onto the surface of the skin, immediately after which a tyne-like device was placed in contact with this solution and used to puncture the skin. This tyne-like device consisted of seven metal 34 g needles of 1 mm length, similar to commercially available devices used in allergen testing. Adjacent skin sites were treated with the microarray or the tyne-like puncturing device in the absence of histamine in order to monitor skin reactions due to the devices rather than the effects of histamine. Additional controls included skin sites treated with histamine topically in the absence of abrasion or puncture. Skin sites were monitored for immediate inflammatory reactions including redness, swelling and the appearance of a wheal-and-flare.

Vigorous inflammatory reactions were observed at skin sites treated with histamine via the solid microneedle array.

Severe erythema and swelling (up to 2 mm of raised tissue) were observed across the entire area of histamine treated skin, whereas sites treated with the device in the absence of histamine displayed only mild redness along the path of abrasion in the complete absence of swelling. Similarly intense reactions were observed with both liquid and reconstituted powder histamine formulations. Skin sites treated with the histamine solution using the tyne-like puncturing device also displayed severe erythema and swelling, although the response was localized to the points of contact of the tynes and the immediate surrounding area. Skin sites treated topically with histamine solution In the absence of abrasion or puncture were not inflamed and appeared indistinguishable from normal, untreated skin.

Histamine dihydrochloride is used in the art as a model system for evaluation of peptide and polypeptide allergens. These results indicate that the described protocol of simultaneous abrasion and delivery can be effectvely used for the topical administration of allergens which are amino adds or amino acid derivatives, and predict similar results for delivery of peptide or polypeptide allergens. Benefits of allergen delivery by microabrasion compared to skin puncture include distribution of the substance to a wider surface area of the skin, thus increasing the reactogenic site compared to the localized distribution accomplished using puncture with tyne-like devices. The increased area of distribution, combined with beter targeting of the highly immune-stimulatory epidermal tissue may increase the sensitivity of allergen testing compared to current tyne-based skin puncture testing methods. In addition, by targeting the shallow epidermal tissue above the capillary beds and peripheral nerve net, delivery according to the current invention is likely to be less invasive and safer than current testing methods.

What is claimed is:

1. A method for the targeted delivery of a vaccine to the epidermal tissue of skin to enhance the immune response comprising simultaneously disrupting only the stratum corneum and delivering the vaccine wherein the vaccine is a powder on an abrading surface of an abrading device to the epidermal tissue of the skin, wherein the disruption of the skin is by abrading the skin with an abrader having a microneedle array which is in contact with the vaccine wherein a reconstituting liquid is separately applied to the skin prior to abrading.

2. The method of claim 1 wherein the vaccine is a DNA vaccine.

3. The method of claim 1 wherein the skin is abraded at least twice.

4. The method of claim 1 wherein the skin is abraded in alternating directions.

5. The method of claim 1 wherein a dry vaccine is reconstituted simultaneously with abrasion.

6. A method for a single and immediate delivery of a reconstituted vaccine treatment to the epidermal tissue of skin to enhance the immune response comprising:
   supplying a substantially dry vaccine which is applied to the skin prior to abrasion;
   abrading the skin with an abrader having a microneedle array of protrusions;
   supplying a reconstituting liquid which substantially reconstitutes the dry vaccine simultaneous with abrasion
   simultaneously disrupting only the stratum corneum but not the epidermis of the skin and delivering the reconstituted vaccine treatment to the epidermal tissue of the skin.

7. The method of claim 6 wherein the vaccine is a DNA vaccine.

8. The method of claim 7 wherein the DNA vaccine encodes an antigen.

9. The method of claim 8 wherein expression of the antigen produces an immune response.

10. The method of claim 6 wherein the skin is abraded at least twice.

11. The method of claim 10 wherein the skin is abraded at least six times.

12. The method of claim 11 wherein the skin is abraded six to twelve times.

13. The method of claim 6 wherein the skin is abraded in alternating directions.

* * * * *